United States Patent [19]
Dunn

[11] Patent Number: 5,830,999
[45] Date of Patent: Nov. 3, 1998

[54] STABILIZATION OF INSULIN THROUGH LIGAND BINDING INTERATIONS

[75] Inventor: Michael F. Dunn, Riverside, Calif.

[73] Assignee: Regents of the University of California, Oakland, Calif.

[21] Appl. No.: 378,412

[22] Filed: Jan. 26, 1995

[51] Int. Cl.⁶ .............................. A61K 38/28; C07K 5/00; C07K 7/00; C07K 16/00
[52] U.S. Cl. .......................... 530/303; 530/304; 530/305; 514/2; 514/3; 514/4
[58] Field of Search ....................... 514/2, 3, 4; 530/303, 530/304, 305

[56] References Cited

U.S. PATENT DOCUMENTS 5,541,155  7/1996  Leone-Bay et al. ......................... 514/2

FOREIGN PATENT DOCUMENTS

WO 91/09617  7/1991  WIPO ........................................ 37/26

OTHER PUBLICATIONS

Brange, J. et al., (1986) In *Subcutaneous Insulin Therapy: Galenics of Insulin Preparations* (M. Berger, Ed.), Springer Verlag, Berlin, Chapter 3, pp. 1–71.
Krayenbühl, C. & Rosenberg, T. (1946) *Rep. Steno Hosp. (Chp.)* 1, 60–73.
Hallas–Moller, K. et al. (1951) *Ugeskr Laeger (Danish)* 113, 1761–1767.
Hallas–Moller, K. (1956) *Diabetes* 5, 7–14.
Derewenda, U. et al. (1989) *Nature* 338, 594–596.
Smith, G.D. and Dodson, G. G. (1992a) *Biopolymers* 32, 441–445.
Smith, G. D. and Dodson, G. G. (1992b) *Proteins: Struct. Func. Genet.* 14, 401–408.
Smith G. D. et al. (1984) *Proc. Natl. Acad. Sci. USA* 81, 7093–7097.
Bentley, G. A. et al. (1976) *Nature* 261, 166–68.
Derewenda, U. et al. (1991) *J. Mol. Biol.* 220, 425–433.
Kaarsholm, N.C. et al. (1989) *Biochemistry* 28, 4427–4435.
Roy, M. et al. (1989) *J. Biol. Chem.* 264, 19081–19085.
Brader, M. L. et al. (1990) *J. Biol. Chem.* 265, 15666–15670.
Brader, M. L. et al. (1991) *Biochemistry* 30, 6636–6645.
Choi, W.–J. E. et al.(1993) *Biochemistry* 32, 11638–11645.
Brader, M. L. et al. (1992) *J. Am. Chem. Soc.* 114, 4480–4486.
Brader, M. L., et al. (1992) *Biochemistry* 31, 4691–4696.
Blundell, T. et al. (1972) *Adv. Protein Chem.* 26, 279–402.
Baker, E. N. et al. (1988) *Phil Trans. Roy. Soc. (London)* B 319, 369–456.
Bentley, G. A. et al. (1992) *J. Mol. Biol.* 228, 1163–1176.
Dodson, E.J. et al. (1979) *Can. J. Biochem.* 57, 469–479.
Galloway, John A. et al, (1990) *Diabetes Mellitus, Theory & Practice*, 4691–4696.
Heine, Robert E. (1993) *The Diabetes Annual* 7, 284–302.
Marble, Alexander (1985) *Joslin's Dabees Mellitus*, Lea & Febiger, PA, 380–405.
Brzovic, PS et al (1994) *Biochemistry* 33, 13057–13069.
Brange J et al.(1992) *Acta Pharm. Nord.* 4, 149–158.
Baker, E.N., et al., *Phil. Trans. R. Soc. Lond.*, B319:369–456 (1988).
Bentley, G.A., et al., *Nature*, 261:166–168 (1976).
Bentley, G.A., et al., *J. Mol. Biol.*, 228:1163–1176 (1992).
Blundell, T., et al., *Adv. Protein Chem.*, 26:279–402 (1972).
Brader, M.L., et al., *Biochemistry*, 31:4691–4696 (1992).
Brader, M.L., et al., *J. Am. Chem. Soc.*, 114:44801–4486 (1992).
Derewenda, U., et al.*Nature*, 338:594–596 (1989).
Derewenda, U., et al., *J. Mol. Biol.*, 220:425–433 (1991).
Hallas–Moeller, K., et al., *Ugeskrift for Laeger,* 113:1761–1767 (1951) (Danish).
Hallas–Moeller, K., *Diabetes*, 5:7–14 (1956).
Krayenbühl, C., et al., *Rep. Steno Mem. Hosp. (Chp.)*, 1:60–73 (1946).
Roy, M., et al., *J. Biol. Chem.*, 264:19081–19085 (1989).
Smith, G.D., et al., *Proc. Natl. Acad. Sci USA*, 81:7093–7097 (1984).
Smith, G.D., et al., *Proteins: Struc., Funct. & Genet.*, 14:401–408 (1992).
Smith, G.D., et al., *Bipolymers*, 32:441–445 (1992).

*Primary Examiner*—Robert J. Hill, Jr.
*Assistant Examiner*—Jennifer Harle
*Attorney, Agent, or Firm*—Fulbright & Jaworski, LLP

[57] ABSTRACT

Insulin formulations containing ligands for the insulin hexamer which bind several orders of magnitude more tightly to the hexamer than chlorine ion or acetate ion. These ligands are aliphatic and aromatic carboxylates having a dissociation constant ($K_D$) of less than about 5 mM, and preferably less than about 1 mM. The increased tightness of binding conveys additional stability to the insulin hexamers, improving their usefulness in slow release and fast acting formulations (for example, for the treatment of diabetics).

6 Claims, No Drawings

STABILIZATION OF INSULIN THROUGH LIGAND BINDING INTERATIONS

BACKGROUND OF THE INVENTION

The present invention relates generally to the fields of biology, chemistry and medicine. More particularly, the present invention is directed to stabilized formulations of insulin and methods for the preparation thereof.

Insulin from sheep, pigs and humans (as the recombinant protein) is used in various commercial preparations to treat diabetes (especially in the Type I or insulin-dependent diabetic). Insulin and insulin derivatives are currently available in both fast acting and slow release formulations. The slow release preparations are solid suspensions (either crystalline or amorphous) of the zinc insulin hexamer. The fast acting forms are soluble preparations that usually are equilibrating mixtures of monomeric, dimeric, tetrameric, hexameric and higher aggregate forms of insulin and insulin derivatives (constructed by site-directed mutagenesis or by synthetic methods) that are rapidly taken up into the blood stream. Both slow release and fast acting forms are usually administered by subcutaneous injection.

The stabilization of various hexamer preparations is brought about through binding interactions between the insulin hexamer and ligands. Therefore, three types of molecules have conventionally been employed: (a) chloride and/or acetate ions; (b) phenolic compounds (phenol, m-cresol or methylparaben); and (c) spermine from salmon. Chloride ion or acetate ion together with phenolic compounds (phenol, m-cresol and methylparaben) are used in the known NPH and Lente insulin formulations [Brange, J. et al., (1986) *In Subcutaneous Insulin Therapy: Galenics of Insulin Preparations* (M. Berger, Ed.), Springer Verlag, Berlin, Chapter 3, pp. 1–71; Krayenbühl, C. & Rosenberg, T. (1946) *Rep. Steno Hosp. (Cph.)* 1, 60–73; Hallas-Moller, K. et al. (1951) *Ugeskr Laeger (Danish)* 113, 1761–1767; Hallas-Moller, K. (1956) *Diabetes* 5, 7–14] as ligands to the insulin hexamer to exert stabilizing interactions on the hexamer.

Crystal structure studies [Derewenda, U. et al. (1989) *Nature* 338, 594–596; Smith, G. D. and Dodson, G. G. (1992a) *Biopolymers* 32, 441–445; Smith, G. D. and Dodson, G. G. (1992b) *Proteins: Struct. Func. Genet.* 14, 401–408; Smith, G. D. et al. (1984) *Proc. Natl. Acad. Sci. USA* 81, 7093–7097; Bentley, G. A. et al. (1976) *Nature* 261, 166–168; Derewenda, U. et al. (1991) *J. MoL BioL* 220, 425–433] and solution studies [Kaarsholm, N.C. et al. (1989) *Biochemistry* 28, 4427–4435; Roy, M. et al. (1989) *J BioL Chem.* 264, 19081–19085; Brader, M. L. et al. (1990) *J BioL Chem.* 265, 15666–15670; Brader, M. L. et al. (1991) *Biochemistry* 30, 6636–6645; Choi, W. -J. E. et al. (1993) *Biochemistry* 32, 11638–11645; Brader, M. L. et al. (1992) *J Am. Chem. Soc.* 114, 4480–4486; Brader, M. L. et al. (1992) *Biochemistry* 31, 4691–4696] have shed considerable light on the nature of the interactions between phenolic molecules and anions that contribute stabilizing interactions to the insulin hexamer. X-ray crystallographic studies of the zinc insulin hexamer have characterized three quite different conformations of the protein [see, e.g., Blundell, T. et al. (1972) *Adv. Protein Chem.* 26, 279–402; Baker, E. N. et al. (1988) *Phil Trans. Roy. Soc. (London) B* 319, 369–456; Bentley, G. A. et al. (1992) *J. Mol Biol.* 228, 1163–1176; and the crystal structure studies cited supra]. These quaternary conformations have been designated $T_6$, $T_3R_3$ and $R_6$ on the basis of their ligand binding properties, allosteric properties and symmetries [Kaarsholm et al. (1989), supra]. The $T_3R_3$ and $R_6$ forms are the predominant species found in the slow-release (prolonged acting) NPH and Lente formulations [Brange et al. (1986), supra].

The $T_6$ and $R_6$ forms each have one exact threefold symmetry axis and three approximate dyad axes. The approximate dyad axes are the consequence of relatively small conformational differences in each asymmetric dimeric unit of the hexamer. The T and R conformations are characterized by remarkable differences. In the T-state, residues 1–8 of the insulin B chain take up an extended conformation; in the R-state, these residues are coiled in an alpha-helical conformation. The interconversion of T to R is accompanied by an approximately 30 Angstrom motion of the phenyl ring of PheB1.

The HisB10 zinc sites of the insulin hexamer are located 16 Angstroms apart on the threefold symmetry axis. In the $T_6$ hexamer, the zinc ion resides in an octahedral ligand field consisting of the imidazole rings of three HisB10 residues and three water molecules. In the $R_6$ hexamer, the new alpha-helical segments pack in around the HisB10 sites and constrain the metal ion geometry to a tetrahedral or five-coordinate geometry. In addition to the coil-to-helix transition, there are smaller differences in conformation throughout the remainder of the B chain and throughout the A chain. These differences are small, and, except for residues B1–B8, the remainder of the B chain and the A chain exhibit very similar folding in the T- and R- states.

The conversion of residues B1–B8 to a helical structure creates a hydrophobic cavity in each subunit at the monomer-monomer interface of each asymmetric dimer (the so-called phenolic pockets). These pockets are large enough to accommodate a wide variety of small organic molecules, including phenol and various substituted phenols [Brader et al. (1991), supra; Choi et al. (1993), supra; Derewenda et al. (1989), supra]. The conversion of $T_6$ to $R_6$ is driven by the binding of ligands, both to the R-state phenolic pockets and to the fourth ligand position on each metal ion.

In the stabilized $R_6$ form, the hexamer is coordinated with six phenolic ligands and two other (e.g., chloride or acetate) ligands. Solution studies have established that there are strong positive heterotropic interactions in the R-state between the phenolic pockets and the fourth ligand position on each metal ion. The synergism between these two classes of sites can greatly stabilize the R-state hexamer.

The $T_3R_3$ form of the hexamer is characterized by a single three-fold symmetry axis [Smith et al. (1984), supra]. As implied by the designation $T_3R_3$, the hexamer is made up of asymmetric dimeric units wherein each dimer contains one insulin molecule in a T-conformation and the other in an R-conformation. The head-to-tail constellation of subunits in each dimer gives a hexamer in which one end of the cylindrical structure has the T conformation (a $T_3$ unit) while the other end has an R conformation (an $R_3$ unit). The $T_3$, end of the hexamer has an octahedral HisB10 zinc site similar to that of the $T_6$ state. Depending on the conditions of crystallization and the exogenous ligands present, the $R_3$ end either has a single tetrahedral zinc site that resides on the threefold axis like that of the $R_6$ state, or there are three new off- axis metal ion sites that involve HisB5 and an alternative conformation of the HisB10 residues. These off-axis sites have only been reported in the $T_3R_3$ species crystallized from 6% sodium chloride in citrate buffer at pH between 6 and 7; therefore, for most practical purposes $T_3R_3$ hexamers may be viewed as comprising a single tetrahedral zinc site (corresponding to one of the two present in the $R_6$ conformation) for coordination with suitable ligands.

The commercially-available slow release formulations of insulin comprise suspensions of amorphous insulin precipitates, insulin crystals or mixtures of precipitates and crystals that typically are injected subcutaneously. The prolonged action of these formulations is believed due to delayed absorption of the injected precipitate/crystalline suspension [Brange et al. (1986), supra].

It would clearly be desirable to provide insulin formulations in which the stability of insulin preparations is extended relative to the currently-available formulations. In addition, the use of formulations with which the absorption of insulin is further delayed would permit a corresponding reduction in the frequency at which the formulations are administered to a patient.

It is an object of the present invention to provide insulin formulations of improved stability and methods for the preparation thereof.

SUMMARY OF THE INVENTION

In accordance with the present invention, insulin formulations are provided comprising ligands for the insulin hexamer which bind tightly to the hexamer, and preferably one or more orders of magnitude more tightly to the hexamer than acetate ion. These ligands are selected from the group consisting of aliphatic and aromatic carboxylates having a dissociation constant ($K_D$) of less than about 5.0 mM, and preferably less than 1.0 mM (the $K_D$ of chloride ion). This increased tightness of binding conveys additional stability to the insulin hexamer and, therefore, imparts improved properties to the hexamer that will improve its usefulness both in slow-release and fast acting formulations for the treatment of diabetics.

DETAILED DESCRIPTION OF THE INVENTION

In accordance with the present invention, advantage is taken of the fact that factors which retard the rate at which the precipitate/crystals dissolve and dissociate to yield biologically active monomeric insulin determine how protracted is the absorption of insulin after injection. The more stable the precipitate or crystals, the greater the physical stability of the preparation toward denaturation, chemical degradation, and/or fibrillation [Brange et al. (1986), supra]. It has been established that both denaturation and fibril formation occur via the insulin monomer [Brange et al. (1986), supra]. In addition, the hexamer is less labile to degradation by bacterial contamination than the insulin monomers [Brange et al. (1986), supra]. Therefore, hexamerization and crystallization greatly stabilize insulin and thereby retard these processes deleterious to the biological activity of insulin formulations.

Further, with the binding of appropriate ligands the $T_3R_3$ and $R_6$ forms of insulin are more stable than the $T_6$ form. Therefore, the allosteric effects of phenolic compounds that bind to the R-state protein pockets and anions that bind to the HisB10 metal sites are very important to the stabilization of insulin preparations.

In accordance with the present invention, it has been determined that certain aliphatic and aromatic organic carboxylic acids (in the form of the carboxylate anions) bind tightly and highly specifically to the two HisB10-bound zinc ions of the Zn(II)—$R_6$ hexamer and to the zinc site at the $R_3$ end of the $T_3R_3$ hexamer. Selected to take into account the 3-dimensional structure of the insulin hexamer, these organic carboxylates have structures which form stronger bonding interactions with the protein and stronger inner-sphere coordination bonds to the zinc ions at each HisB10 site relative to the conventionally-employed acetate ions.

Use of organic carboxylates in accordance with the present invention may also provide stabilized hexamers with superior characteristics when used in preparations in which the insulin is crystallized or precipitated. Finally, some of the carboxylates employed in accordance with the present invention may have superior antimicrobial effects relative to chloride and/or acetate.

Pursuant to one aspect of the present invention, functional groups may be incorporated into the design of the organic carboxylates that specifically interact with protein residues, thus forming weak bonding interactions (favorable van der Waals contacts, hydrogen bonding interactions and dipole interactions). Such functional groups include, but are not limited to, the following: hydroxyl, amino, nitro or amido.

Pursuant to another aspect of the present invention, electron releasing groups that increase the density of negative charge on the carboxylate group and thus increase the affinity of the organic carboxylate ligand for the HisB10 metal ion may also suitably be incorporated. Suitable electron releasing groups include, but are not limited to, the following: hydroxylate anion, thiolate anion, hydroxyl, methoxyl, amino and alkyl.

The use of ligands in accordance with the present invention provides strong stabilizing interactions that decrease the rate at which the insulin hexamer dissociates. Because the insulin monomer is a much more labile species than the hexamer toward denaturation, fibril formation and degradation by chemical reaction or by bacterial contamination, ligand interactions that stabilize the hexamer enable the preparation of insulin formulations with improved stabilities. This stabilizing effect is also important for insulin derivatives, wherein the hexameric species have lower stabilities than do the wild type human, pig or cow or sheep insulins.

Preferred organic carboxylic acids employed (in the form of the corresponding carboxylates) as ligands in accordance with the present invention show significantly increased affinities for the $R_6$ and/or $T_3R_3$ conformations of the zinc-insulin hexamer. This is reflected by a dissociation constant $K_D$ of less than about 1.0 mM (relative to 37.6 mM for acetate and 1.0 mM for chloride) for the preferred ligands of the invention. In some embodiments, this is a consequence of weak bonding interactions between substituents (functional groups) on the organic carboxylate ion and the protein at the HisB10 sites. In addition, improved inner sphere coordination of the carboxylate ion to the HisB10 bound zinc ion in some embodiments causes these ligands to bind more tightly to the hexamer. This tight binding stabilizes the hexamer and thus decreases the rate of insulin degradation by denaturation, chemical attack, and the action of bacteria. These interactions increase the affinities of these ligands by several orders of magnitude in comparison to the binding of acetate ion and by more than one order of magnitude in comparison to chloride ion.

In accordance with preferred embodiments of the present invention, particular classes of organic carboxylates have been found to bind particularly tightly. A first preferred type comprises aliphatic organic carboxylates comprising at least 5 carbon atoms. Exemplary embodiments in this class include, but are not limited to, carboxylates derived from the following acids: valeric, heptanoic, octanoic, nonanoic, lauric, and their branched chain and unsaturated derivatives, and 1-adamantanecarboxylic acid. Additional members of this large class include aliphatic carboxylic acids with substituents along the chain that are either nonpolar (e.g., alkyl) or polar (e.g., hydroxyl, amido or halo). Preferred embodiments of this class are straight chain fatty acids with chain lengths $>C_8$; the hydrophobic chains of the fatty acids make favorable van der Waals contacts with the hydrophobic residues that line the interior of the tunnel.

One preferred subclass of aliphatic carboxylic acids are those incorporating a three-fold symmetry element into the organic portion of the molecule that complements the three-fold symmetry of the HisB10 sites. Examples of this subclass include the carboxylates derived from trialkylacetic acids, such as trimethylacetic acid and symmetric derivatives thereof containing polar substituents such as tris-hydroxymethylacetic acid or tris (2-hydroxyethyl) acetic acid, and adamantane-1-carboxylic acid.

The HisB10 anion sites (two in the $R_6$ hexamer, one in the $T_3R_3$ hexamer) are 8 to 12 Angstrom long tunnels formed at the interstices of three insulin dimers arranged at an end of the hexamer. Since the protein surfaces at these sites are partially hydrophobic, the three-fold symmetries of the hydrophobic trialkyl group of a trialkyl acetate ion and the hydrophobic adamantine ring system of adamantane-1-carboxylate match the three-fold symmetry of the sites. This matching of symmetry helps to maximize favorable van der Waals contacts between ligand and site.

A second class of ligands suitable for use in accordance with the present invention comprises aromatic carboxylates. Preferably, the aromatic carboxylates bear hydrophobic and/or hydrophilic substituents spaced to maximize hydrophobic, hydrogen bonding and/or dipolar interactions with residues that form the surface of the tunnels to increase the affinity between site and ligand. In general, by aromatic carboxylate in accordance with the present invention is meant a carboxylate derived from a carboxylic acid comprising at least one homoaromatic or heteroaromatic ring. Suitable aromatic ring systems include, but are not limited to, the following: phenyl, naphthyl, pyridyl, pyrrolyl, imidazolyl, indolyl and 4-oxo-1,4-pyranyl. Exemplary embodiments include carboxylates derived from the compounds listed in Table I and analogs thereof (e.g., position isomers of the particular compounds listed). Preferred embodiments having particularly strong binding properties include carboxylates derived from 4-hydroxy-3-nitrobenzoic acid, 3-indoleacrylic acid and p-dimethylaminocinnamic acid.

Each tunnel is lined with hydrophobic residues (e.g., the three side chains of ValB2 and the three Leu side chains from LeuB6), six polar groups (three carboxamide side chains from AsnB3 and three carboxamide side chains from GlnB4), and the three backbone NH groups of CysB7). There is considerable flexibility in the tunnel structure. The Asn carboxamides can assume a conformation that forms a cap or dome-like covering to the tunnel, or these residues can be folded away leaving the tunnel open [Smith & Dodson (1992a,b), supra]. Therefore, for example, the 3-nitro group and the 4-phenolate oxygen of 4-hydroxy-3-nitrobenzoate or the indole ring of 3-indoleacrylic acid can form stabilizing hydrogen bonds to the carboxamine group (s) of AsnB3. The ligand carboxylate may coordinate to the HisB10 zinc ion in an asymmetric orientation which places one carboxylate oxygen within H-bonding distance of the amide NH of a CysB7 residue.

Table 1 lists representative organic carboxylates from these classes of ligands and compares the relative affinities of these compounds for the zinc $R_6$ insulin hexamer to the affinities of chloride ion and acetate ion. This comparison shows that acetate ion binds less tightly than do the various organic carboxylate ions contemplated herein as within the scope of the invention, and that preferred ligands in accordance with the present invention bind substantially more tightly than does chloride ion.

TABLE I

| Acids of Invention | $K_D$ (mM) |
|---|---|
| Lauric Acid | 0.28 |
| Nonanoic Acid | 0.62 |
| Octanoic Acid | 0.73 |
| Heptanoic Acid | 0.90 |
| Valeric Acid | 3.36 |
| 1-Adamantanecarboxylic Acid | 0.45 |
| Trimethylacetic Acid | 1.96 |
| 3-nitro-4-hydroxybenzoic Acid | 0.04 |
| 4-amino-3-hydroxybenzoic Acid | 0.12 |
| m-nitrobenzoic Acid | 0.16 |
| p-hydroxybenzoic Acid | 0.20 |
| p-aminobenzoic Acid | 0.22 |
| p-acetamidobenzoic Acid | 0.27 |
| Benzoic Acid | 0.28 |
| 3-amino-4-hydroxybenzoic Acid | 0.31 |
| 3-hydroxy-4-nitrobenzoic Acid | 0.33 |
| 3,5-dinitrobenzoic Acid | 0.36 |
| Isophthalic Acid | 1.22 |
| 2-methyl-3-nitrobenzoic Acid | 2.83 |
| 3-Indoleacrylic Acid | 0.08 |
| p-Dimethylaminocinnamic Acid | 0.13 |
| Indole-3-Carboxylic Acid | 0.25 |
| Nicotinic Acid | 0.38 |
| 4-Hydroxycinnamic Acid | 0.43 |
| 3-(3'-Pyridyl)acrylic Acid | 0.48 |
| 3-Nitrocinnamic Acid | 0.57 |
| 2-Naphthylacetic Acid | 0.88 |
| Isonicotinic Acid | 1.00 |
| Urocanic Acid | 1.24 |
| p-Hydroxy Phenylacetic Acid | 2.24 |
| Coumalic Acid | 5.51 |
| Control Anions | |
| Propionate | 11.2 |
| Acetate | 21.1 |
| Chloride | 1.0 |

In accordance with another aspect of the present invention, methods for preparation of stabilized insulin compositions are provided. In one embodiment, at least one organic carboxylate in accordance with the present invention is introduced into a composition comprising insulin hexamers stabilized by chloride or acetate. Chloride ion and acetate ion are replaced by one of the more tightly binding organic carboxylates. Alternatively (for example, when using recombinant insulin preparations), at least one organic carboxylate in accordance with the present invention and a stabilizing amount of a phenolic compound (e.g., phenol, m-cresol, methylparaben) are added to a solution of non-stabilized insulin. Because these ligands bind more tightly, lower phenolic ligand concentrations can be used in the formulations to achieve the same or higher stability; therefore, compositions prepared by adding a stoichiometric amount of organic carboxylate in accordance with the present invention are substantially more stable than the corresponding compositions wherein the ligand is chloride or acetate. The ratio of phenolic compound to insulin hexamer currently employed is on the order of about 22 phenolic molecules per hexamer.

While the amount of ligand required to provide a composition having improved stability relative to prior art formulations will depend upon the choices of anionic ligand and phenolic ligand (and, in particular, upon the affinity of these ligands for the insulin complex), in general the present invention contemplates that the compositions comprise at least about 100% of the stoichiometric amount of ligand for the available ligand sites in the insulin formulation, and in some instances at least about 1000% of the stoichiometric amount. For any given formulation, the appropriate concentration of ligands may readily be determined empirically.

One class of formulations of interest in accordance with the present invention are soluble, fast-acting insulin preparations at neutral pH. Formulation of rapid-acting insulins of enhanced stability varies with respect to insulin species (human, pork, beef, sheep, genetically modified human, etc.) and with respect to the isotonic agent(s) used, the buffering substance, and the pH. The preparation of such formulations would be routinely effected by those skilled in the art. In general, these preparations comprise insulin concentrations below the solubility limit of the hexameric species (i.e., $T_3R_3$ or $R_6$); insulin concentrations employed depend strongly on the pH of the preparation, as pH determines solubility. In addition, the compositions have a $Zn^{2+}$ to insulin ratio of no less than about 2 $Zn^{2+}$ per insulin hexamer; while higher ratios (e.g., up to about 4 $Zn^{2+}$ per hexamer) may be of use in some instances to take advantage of the antimicrobial effects of high zinc concentrations, at higher ratios the solubility of the insulin hexamer is decreased.

A suitable organic carboxylate is added in a ratio of at least 1 per hexamer in the case of $T_3R_3$ preparations and at least 2 per hexamer in the case of $R_6$ preparations. For either formulation, the ratio of the carboxylate to the insulin hexamer is adjusted to achieve the desired level of stability; ratios as high as 10 to 1,000 may be required to give the desired level of stability. In contrast to prior art formulations, neither chloride ion nor acetate ion is used in these preparations.

A suitable phenolic compound (e.g., phenol, methylparaben or m-cresol) is also generally added in a ratio of at least about 3 per insulin hexamer in the case of $T_3R_3$ preparations and at least 6 per hexamer in the case of $R_6$ preparations. In accordance with the present invention, the stability advantage conveyed by the carboxylate ligand for the HisB10 site(s) permit the use of lower concentrations of the phenolic compound than would in general be required in current commercial preparations (i.e., about 22 phenolic molecules per hexamer), although the use of larger amounts of the phenolic compound may be appropriate in some formulations. In particular instances, the more tightly binding carboxylates (e.g., 3-nitro-4-hydroxybenzoate, m-nitrobenzoate) are capable of forming $T_3R_3$ hexamers without the addition of any phenolic compound, and these carboxylates give $R_6$ hexamers of certain insulin mutants (e.g., human E-B13Q) without the addition of phenolic compounds.

For fast acting preparations, glycerol is commonly used as an isotonic agent; however, other isotonic agents as are known in the art would be equally suitable. Neutral pH preparations can be formulated without the need for a buffering agent. The carboxylates used as ligands for the HisB10 site(s) provide some weak buffering capacity; most of the buffering is provided by the insulin. These formulations typically fall into the pH range of about 6.5 to 8.

A second class of formulations of interest in accordance with the present invention includes insoluble, protracted (slow release) insulin formulations at mildly acidic pH. Formulation of slow release, insoluble insulin preparations of enhanced stability also varies with respect to insulin species, zinc content, preservative(s), isotonic agent(s), buffering substance(s) and precipitating and/or crystallizing agent(s). In such formulations, insulin concentrations which exceed the solubility limit of the hexameric species are utilized. A $Zn^{2+}$ to insulin ratio of no less than 2 $Zn^{2+}$ per insulin hexamer is typically employed; higher ratios may be helpful in reducing the solubility of insulin and contributing an antimicrobial effect. An isotonic agent (for example, glycerol) is used in some compositions; in others, the organic carboxylate ligand for the HisB10 site(s) also functions as the isotonic agent.

A suitable organic carboxylate in accordance with the present invention is added to stabilize the insoluble hexamers through binding to the HisB10 site(s). Typically, the ligand is added in a ratio of at least 1 per hexamer in the case of $T_3R_3$ preparations and at least 2 per hexamer in the case of $R_6$ preparations. For either formulation, ratios as high as 10 to 1,000 may be necessary to achieve the level of stability needed. Advantageously, the organic carboxylate ligand for the HisB10 site(s) also helps provide the buffering needed to attain the desired pH at which crystallization and/or precipitation occurs. The buffering properties of insulin also contribute to the buffering needed. The insoluble preparations are generally formulated at a pH in the range of about 4.0 and about 7.5. In general, neither chloride nor acetate ion is needed in these preparations, although in some instances these ions may be employed to induce crystal growth or precipitation; their function as stabilizing agents is typically carried out by the organic carboxylate employed as ligand in accordance with the present invention.

Finally, as in the fast acting formulations, a suitable phenolic compound (e.g., phenol, methylparaben or m-cresol) usually is added in a ratio of at least about 3 per insulin hexamer in the case of $T_3R_3$ preparations and at least 6 per hexamer in the case of $R_6$ preparations. In accordance with the present invention, the stabilizing effects of the carboxylate ligand for the HisB10 site(s) permit the use of lower concentrations of the phenolic compound than would in general be required in current commercial preparations. As noted above for the soluble preparations, the tightest binding carboxylates are capable of forming $T_3R_3$ and $R_6$ species without the addition of phenolic compounds.

In addition to the conventional fast acting and slow release formulations, in some instances it is desirable to provide mixtures of rapid acting and protracted acting insulins. To achieve such mixtures, mutual compatibility must be present. If the two forms are premixed immediately prior to injection, slow changes resulting from physical instability (due to precipitation or dissolving) can often be tolerated. Otherwise, conventional formulation techniques as are known in the art may suitably be employed to provide useful mixtures.

Many of the organic carboxylates contemplated for use in accordance with the present invention are naturally-occurring products (e.g., p-aminobenzoic acid, cinnamic acid, the straight chain fatty acids) which may routinely be employed to provide products with minimal or no toxic side effects. Moreover, the range of affinities exhibited by the carboxylates of the invention enables the preparation of insulin formulations having a wide range of rates of release of the hexamer. For example, the most tightly binding ligands could be used in high concentration to prepare soluble slow-release insulin formulations, while less-tightly binding ligands and/or lower ligand concentrations would provide faster-acting compositions.

What is claimed is:

1. A composition comprising insulin hexamers, said hexamers having a $T_3R_3$ or $R_6$ conformation, said conformation stabilized by at least one ligand having a dissociation constant $K_D$ of less than about 5 mM, said ligand being selected from the group consisting of aliphatic carboxylic acids or their salts comprising aliphatic acids of at least 5 to 12 carbon atoms and aromatic carboxylic acids or their salts, wherein the aromatic carboxylic acids or their salts comprise at least one aromatic ring selected from the group consisting of phenyl, naphthyl, pyrrolyl imidazolyl, indolyl and 4-oxo-1.4-pyranyl and wherein the aliphatic carboxylic acids or aromatic carboxylic acids can be substituted with hydroxylate anion, thiolate anion, hydroxy, methoxy, amino, alkyl, nitro, or amido groups.

2. A composition according to claim 1, wherein the ligand has a dissociation constant $K_D$ of less than about 1 mM.

3. A composition according to claim 1, wherein the ligand incorporates a three-fold symmetry element.

4. A composition according to claim 3, wherein the ligand is selected from the group consisting of trialkylacetates and adamantane-1-carboxylate.

5. A composition according to claim 1, wherein the ligand is selected from the group of aliphatic carboxylic acids or their salts comprising at least 8 carbon atoms.

6. A composition according to claim 1, wherein the ligand is an aromatic carboxylic acid or its salt selected from the group consisting of 3-nitro4-hydroxybenzoic acid, 4-amino-3-hydroxybenzoic acid, m-nitrobenzoic acid, p-hydroxybenzoic acid, p-aminobenzoic acid, p-acetamidobenzoic acid, benzoic acid, 3-amino4-hydroxybenzoic acid, 3-hydroxy-4-nitrobenzoic acid, 3,5-dinitrobenzoic acid, 3-indoleacrylic acid, p-dimethylaminocinnamic acid, indole-3-carboxylic acid, 4-hydroxycinnamic acid, 3-nitrocinnamic acid, 2-napthylacetic acid, isophthalic acid, 2-methyl-3-nitrobenzoic acid, urocanic acid, p-hydoxyphenylacetic acid and coumalic acid.

* * * * *

UNITED STATES PATENT AND TRADEMARK OFFICE
CERTIFICATE OF CORRECTION

PATENT NO. : 5,830,999
DATED : November 3, 1998
INVENTOR(S) : Michael F. Dunn

It is certified that error appears in the above-identified patent and that said Letters Patent is hereby corrected as shown below:

| COLUMN | LINE | |
|---|---|---|
| TITLE | | Change "INTERATIONS" to -- INTERACTIONS -- |
| ABSTRACT | 3 | Change "chlorine" to -- chloride -- |
| 1 | 2 | Change "INTERATIONS" to -- INTERACTIONS -- |
| 1 | 47 | Change "MoL" to -- Mol. -- |
| 1 | 47 | Change "BioL" to -- Biol. -- |
| 1 | 50 | Change "BioL" to -- Biol. -- |
| 1 | 51 | Change "BioL" to -- Biol. -- |
| 2 | 52 | After "T$_3$" delete the comma |
| 9 | 7 | Change "1.4" to --1,4 -- |
| 10 | 6 | Change "nitro4" to -- nitro-4 -- |
| 10 | 9 | Change "amino4" to -- amino-4 -- |

Signed and Sealed this

Twenty-ninth Day of June, 1999

Attest:

Q. TODD DICKINSON

*Attesting Officer*  *Acting Commissioner of Patents and Trademarks*